(12) United States Patent
Wetzler et al.

(10) Patent No.: US 7,575,578 B2
(45) Date of Patent: Aug. 18, 2009

(54) SURGICAL DRILL GUIDE

(75) Inventors: Merrick Wetzler, Cherry Hill, NJ (US); Martin Gillespie, New Bern, NC (US)

(73) Assignee: Karl Storz GmbH & Co. KG (DE)

( * ) Notice: Subject to any disclaimer, the term of this patent is extended or adjusted under 35 U.S.C. 154(b) by 1196 days.

(21) Appl. No.: 10/365,904

(22) Filed: Feb. 13, 2003

(65) Prior Publication Data

US 2003/0216742 A1 Nov. 20, 2003

(51) Int. Cl.
*A61B 17/60* (2006.01)

(52) U.S. Cl. .................................. 606/96

(58) Field of Classification Search ............ 606/96–98, 606/87, 102–103, 64
See application file for complete search history.

(56) References Cited

U.S. PATENT DOCUMENTS

| | | | | |
|---|---|---|---|---|
| 4,103,683 A * | 8/1978 | Neufeld | ................. | 606/67 |
| 4,672,957 A | 6/1987 | Hourahane | ................. | 128/92 |
| 4,722,331 A | 2/1988 | Fox | ................. | 128/92 |
| 4,733,654 A | 3/1988 | Marino | ................. | 128/92 |
| 4,739,751 A | 4/1988 | Sapega et al. | ................. | 128/92 |
| 4,781,182 A | 11/1988 | Purnell et al. | ................. | 128/92 |
| 4,883,048 A * | 11/1989 | Purnell et al. | ................. | 606/96 |
| 4,901,711 A | 2/1990 | Goble | ................. | 606/98 |
| 4,911,153 A | 3/1990 | Border | ................. | 606/98 |
| 4,920,958 A * | 5/1990 | Walt et al. | ................. | 606/96 |
| 4,950,271 A | 8/1990 | Lewis et al. | ................. | 606/102 |
| 5,078,719 A * | 1/1992 | Schreiber | ................. | 606/87 |
| 5,112,337 A | 5/1992 | Paulos et al. | ................. | 606/96 |
| 5,154,720 A | 10/1992 | Trott et al. | ................. | 606/96 |
| 5,163,940 A | 11/1992 | Bourque | ................. | 606/96 |
| 5,176,681 A * | 1/1993 | Lawes et al. | ................. | 606/64 |
| 5,234,434 A | 8/1993 | Goble et al. | ................. | 606/96 |
| 5,300,077 A | 4/1994 | Howell | ................. | 606/96 |
| 5,314,429 A | 5/1994 | Goble | ................. | 606/96 |
| 5,320,626 A | 6/1994 | Schmieding | ................. | 606/96 |
| 5,324,295 A | 6/1994 | Shapiro | ................. | 606/86 |
| 5,330,468 A | 7/1994 | Burkhart | ................. | 606/96 |
| 5,334,192 A * | 8/1994 | Behrens | ................. | 606/96 |
| 5,350,383 A * | 9/1994 | Schmieding et al. | ................. | 606/96 |
| 5,385,567 A | 1/1995 | Goble | ................. | 606/96 |
| 5,403,322 A * | 4/1995 | Herzenberg et al. | ................. | 606/98 |
| 5,454,816 A | 10/1995 | Ashby | ................. | 606/88 |
| 5,458,602 A | 10/1995 | Goble et al. | ................. | 606/96 |
| 5,514,144 A | 5/1996 | Bolton | ................. | 606/96 |
| 5,562,664 A * | 10/1996 | Durlacher et al. | ................. | 606/96 |

(Continued)

FOREIGN PATENT DOCUMENTS

FR 2 716 364 2/1994

*Primary Examiner*—Eduardo C Robert
*Assistant Examiner*—James L Swiger
(74) *Attorney, Agent, or Firm*—St. Onge Steward Johnston & Reens LLC

(57) ABSTRACT

A surgical drill guide is disclosed generally comprising a handle connected to an arm, the arm having an end for contacting a bone. The handle has a plurality of non-parallel channels therein for receiving a sleeve at different angles. Once properly positioned, the sleeve can be used to guide a K-wire into the bone, which can then be used as a guide for drilling a tunnel. The various angles allow the surgeon to achieve a range of tunnel lengths. In some embodiments, the guide has a locking mechanism for locking the sleeve in the channels.

8 Claims, 6 Drawing Sheets

U.S. PATENT DOCUMENTS

| | | | |
|---|---|---|---|
| 5,601,566 A | 2/1997 | Dance et al. | 606/86 |
| 5,613,971 A | 3/1997 | Lower et al. | 606/96 |
| 5,643,273 A * | 7/1997 | Clark | 606/96 |
| 5,681,320 A | 10/1997 | McGuire | 606/104 |
| 5,683,400 A | 11/1997 | McGuire | 606/96 |
| 5,688,284 A | 11/1997 | Chervitz et al. | 606/96 |
| 5,891,150 A | 4/1999 | Chan | 606/96 |
| 5,968,050 A | 10/1999 | Torrie | 606/87 |
| 6,019,767 A | 2/2000 | Howell | 606/96 |
| 6,120,511 A | 9/2000 | Chan | 606/96 |
| 6,126,661 A * | 10/2000 | Faccioli et al. | 606/64 |
| 6,187,011 B1 * | 2/2001 | Torrie | 606/96 |
| 6,210,415 B1 | 4/2001 | Bester | 606/96 |
| 6,254,604 B1 | 7/2001 | Howell | 606/96 |
| 6,254,605 B1 * | 7/2001 | Howell | 606/96 |
| 7,077,847 B2 * | 7/2006 | Pusnik et al. | 606/96 |

* cited by examiner

SURGICAL DRILL GUIDE

FIELD OF THE INVENTION

The present invention relates to an apparatus for performing a drilling procedure during surgery. More specifically, the invention relates to an apparatus for guiding a drilling member into a bone at a plurality of possible angles, achieving a range of tunnel lengths.

BACKGROUND OF THE INVENTION

Today, due to widespread engagement in sports and other physical activities, damage to ligaments, cartilage, and tendons in joints has become a relatively common phenomenon. Unfortunately, though this damage often requires surgical repair, the repair of some of these joints can be somewhat difficult.

Examples of such ligaments are the cruciate ligaments, the anterior cruciate ligament (ACL) and the posterior cruciate ligament (PCL). These ligaments of the human knee cooperate with other ligaments and soft tissue to provide static and dynamic stability to the knee joint. Often, the cruciate ligaments are ruptured or torn as a result of physical activity and, consequently, various surgical procedures have been developed for reconstructing the ACL and PCL, thereby restoring normal function to the knee.

For instance, many times, when a person's ACL and/or PCL is significantly damaged, the knee joint is repaired by substituting a harvested or synthetic replacement ligament for the damaged one. In these cases, the graft ligament is extended across the interior of the joint and its two opposite ends are anchored to the femur and tibia bones. Typically, these procedures involve forming tunnels in the femur and tibia bones, then extending the ends of the graft ligament, either part way or all the way, through these bone tunnels, and then securing these ends to the bones, usually by fastening them to either the side walls of the bone tunnels or the exterior surfaces of the bones. Once anchored in place, the graft ligament is able to cooperate with the surrounding tissues and thereby perform the functions of the damaged ACL or PCL.

In order to perform these procedures, surgeons typically use a drill guide to create the tunnels in the femur and tibia bones. These drill guide devices generally include a handle or other support means for holding the device next to the patient's body. Typically, these drill guide devices also include a "probe" arm having a tip that is adapted to be disposed within the knee, often at a location next to what is expected to be one end of the tunnel to be drilled (i.e. the spot where the drilling member that drills the tunnel will exit the bone). Usually, a guide sleeve is provided for directing a drill, or a guidewire for later guiding the drill, into position on the anterior surface of one of the bones surrounding the knee joint. This guide sleeve typically has its axis more or less aligned to intersect with the aforementioned probe tip and is generally slidable or variable in position relative to the support means.

In operation, these known drill guide devices are used by first placing the probe tip at or near a predetermined location on the bone. Next, the drill guide sleeve is adjusted relative to the probe arm so that one end of the guide sleeve is directed toward the appropriate position on the anterior surface of the bone. Once in place, the probe tip and guide sleeve are locked in position relative to each other by various means known in the art, as further explained below. Once the guide sleeve is adjusted and locked in position, a guidewire, often known as a K-wire, is slid through the guide sleeve and advanced through the bone. This K-wire defines the tunnel drilling axis. When the K-wire is seated in position on the bone, the drill guide sleeve is unlocked and removed, longitudinally, back along the K-wire. The rest of the drill guide device is then removed, leaving only the K-wire. At this point, a cannulated drill is slid over the K-wire to drill the tunnel in the bone.

Due to the complex interdependency between the ACL, the PCL, and the other knee ligaments, bones, and tissues, the precise positioning of the graft ligament relative to the surrounding bones is critical to the successful reconstruction of the knee joint. Specifically, the ability of the surgeon to precisely control the positioning and formation of the bone tunnels is of particular importance.

Accordingly, as noted above, these drill guide devices typically include a probe arm and a drill sleeve that are angularly displaceable relative to each other. Examples of such devices are disclosed in U.S. Pat. No. 4,672,957 to Hourahane; U.S. Pat. No. 4,722,331 to Fox; U.S. Pat. No. 4,781,182 to Purnell et al.; U.S. Pat. No. 5,112,337 to Paulos et al.; U.S. Pat. No. 5,154,720 to Trott et al.; and U.S. Pat. No. 5,163,940 to Bourque, U.S. Pat. No. 5,330,468 to Burkhart; U.S. Pat. No. 5,350,383 to Schmieding et al.; U.S. Pat. No. 5,458,602 to Goble et al.; U.S. Pat. No. 5,562,664 Durlacher et al.; U.S. Pat. No. 5,613,971 to Lower et al.; U.S. Pat. No. 5,643,273 to Clark; and U.S. Pat. No. 5,968,050 to Torrie, all of which are hereby incorporated herein by reference.

Typically, the probe arm and the part of the device that holds the drill sleeve, such as a handle, are connected by, or one is mounted on the other with, a mechanism facilitating this relative angular displacement. In most of these devices, this mechanism includes an arcuate piece along which, or through which, another piece can be ratcheted or slid, and subsequently, tightened or locked in a position where the appropriate angular displacement is achieved. Accordingly, the surgeon is able to guide the drilling sleeve against the anterior portion of the bone at a variety of angles by moving the part of the drill guide holding the sleeve arcuately relative to the probe arm. In this way, the operator of the drill guide is able to guide the sleeve against the bone at a particular desired angle for a particular surgical operation.

One disadvantage of these devices, however, is that they typically permit a certain degree of toggling. As a result, the accuracy of the device is reduced. However, as noted above, due to the complex interdependency between the various parts of the knee, precise positioning of the guidewire is crucial to a successful procedure.

Another disadvantage of these devices is that they tend to be difficult to manipulate. Once the probe arm is positioned on the bone, unnecessary movement of the device can cause the tip of the arm to change position. Moreover, excessive movement can even result in damage to the knee. Therefore, once the tip of the arm is in position, the surgeon will want to move the device as minimally as possible while selecting the appropriate angle for the drill sleeve. However, when using the aforementioned devices, it can be difficult for the surgeon, while trying to hold the device steady with one hand, to move the drill sleeve portion of the device to the appropriate angle and then hold it steady while locking it into position. Moreover, the fact that these devices typically employ a number of parts similarly increases the likelihood that undesired movement will occur while the device is being locked into position against the bone.

Another type of device that has been proposed includes a body having a plurality of angularly displaced sockets for receiving the probe, such as that disclosed in U.S. Pat. No. 4,920,958 to Walt et al, which is hereby incorporated herein by reference. However, this device has the disadvantage that, once the probe has been inserted into the knee and positioned on the bone, the angle of the wire guide relative to the probe cannot be changed without having to withdraw, reinsert, and reposition the probe.

What is desired, therefore, is an apparatus for guiding a drilling member into a bone that is easy to manipulate. What is further desired is an apparatus for guiding a drilling member into a bone that reduces undesired movement of the device. What is also desired is an apparatus for guiding a drilling member into a bone that does not needlessly damage the patient's knee.

SUMMARY OF THE INVENTION

Accordingly, it is an object of the present invention to provide a surgical drill guide that reduces the amount of toggling experienced by the device.

It is a further object of the present invention to provide a surgical drill guide that facilitates the easy adjustment of the angle for the drill sleeve, even after the device has been positioned on a bone.

It is yet another object of the present invention to provide a surgical drill guide that minimizes the number of parts required to permit variable angles for the drill sleeve.

To overcome the deficiencies of the prior art and to achieve at least some of the objects and advantages listed, the invention comprises a surgical drill guide, including a handle having a plurality of sleeve channels, each channel having an axis, the axes of at least two of the channels being non-parallel with respect to each other, an arm having a first end connected to the handle and a second end adapted to contact a bone, and at least one sleeve adapted to receive a drilling member, the sleeve being adapted to be inserted into the plurality of sleeve channels in the handle, wherein the angle of the sleeve with respect to the handle is variable by disposing the sleeve in different ones of the plurality of channels.

In another embodiment, the invention comprises a surgical drill guide, including a handle having a plurality of drill member channels, each channel having an axis, the axes of at least two of the channels being nonparallel with respect to each other, an arm having a first end connected to the handle and a second end adapted to contact a bone, and at least one drilling member being adapted to be inserted into any one of the plurality of drill member channels in the handle wherein the angle of the drilling member with respect to the handle is variable by disposing the drilling member in different ones of the plurality of channels.

DETAILED DESCRIPTION OF THE DRAWINGS

Figure 1:
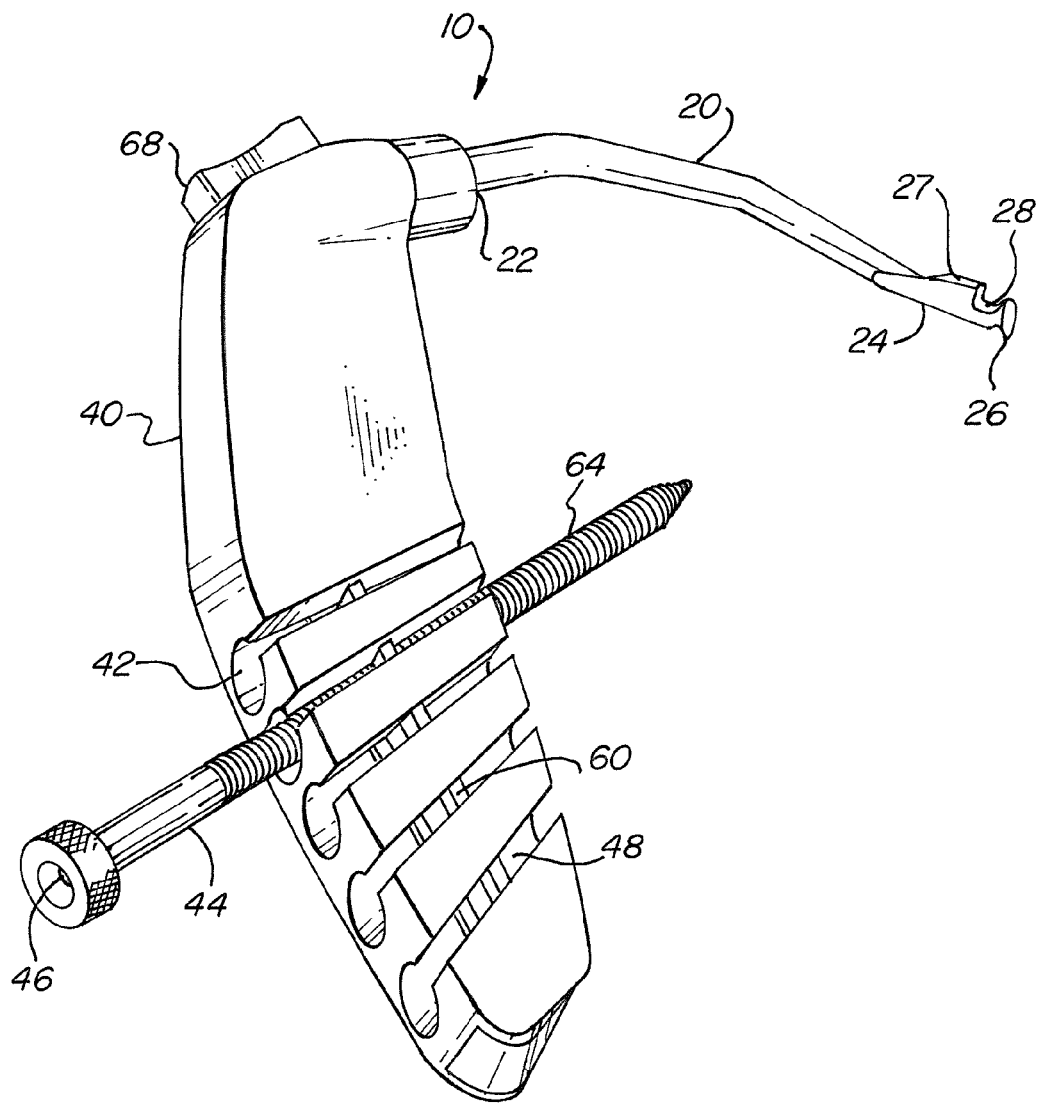
FIG. 1 is a perspective view of a surgical drill guide in accordance with the present invention.

The basic components of one embodiment of a surgical drill guide 10 in accordance with the invention are illustrated in FIG. 1. As used in the description, the terms "top," "bottom," "upper," "lower," "front" and "rear" refer to the objects referenced when in the orientation illustrated in the drawings, which orientation is not necessary for achieving the objects of the invention.

Figure 7:
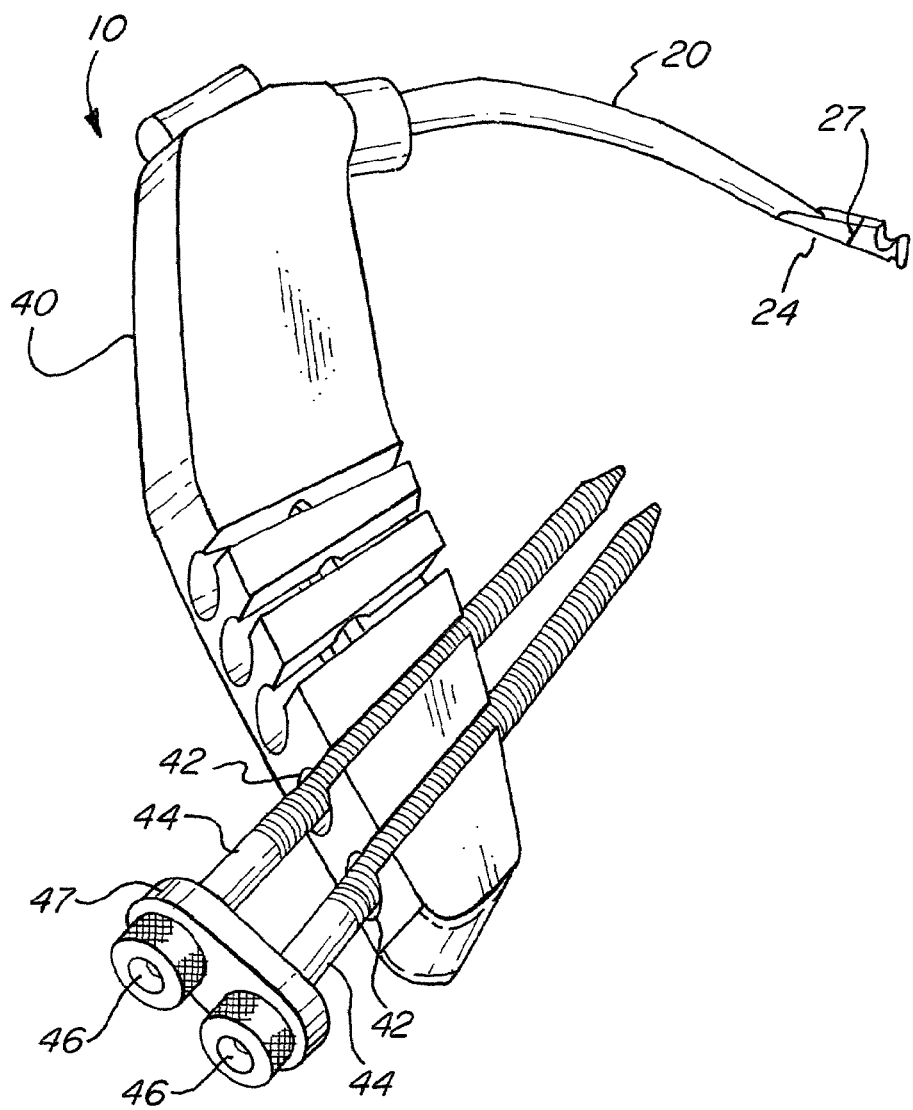
FIG. 7 is another perspective view of a surgical drill guide in accordance with the present invention.

In the embodiment depicted in FIG. 1, a probe arm 20 is connected to a handle 40. A first end 22 of the arm 20 connects the arm 20 to the handle 40, while a second end 24 of the arm 20 is adapted to contact a bone. In certain embodiments, the end 24 includes a hook 26 for hooking onto a particular anatomical structure, such as, for example, the intercondylar notch. In other embodiments, such as depicted in FIG. 7, the end 24 has a mark 27 for aligning the arm 20 with a particular anatomical landmark, such as, for example, the anterior horn of the lateral meniscus. Mark 27 may comprise any modification of at least one surface of the end 24 that indicates to a surgeon that the arm 20 is in the proper location, such as, for example, a line etched via chemical or laser means or created with ink. In certain advantageous embodiments, the end 24 includes an aperture 28, such as an open ended hole, which serves as a target for a drilling member, as is further explained below.

The handle 40 includes a plurality of channels 42 for receiving at least one drill sleeve 44. At least two of the channels 42 are not parallel with respect to each other, such that, when the sleeve 44 is disposed in one of the non-parallel channels 42, its longitudinal axis is angularly displaced from the longitudinal axis of the sleeve 44 when the sleeve 44 is disposed in one of the other non-parallel channels 42. Accordingly, a surgeon using the drill guide device is able to select the angle at which to dispose the sleeve 44 in the handle 40.

Figure 2:
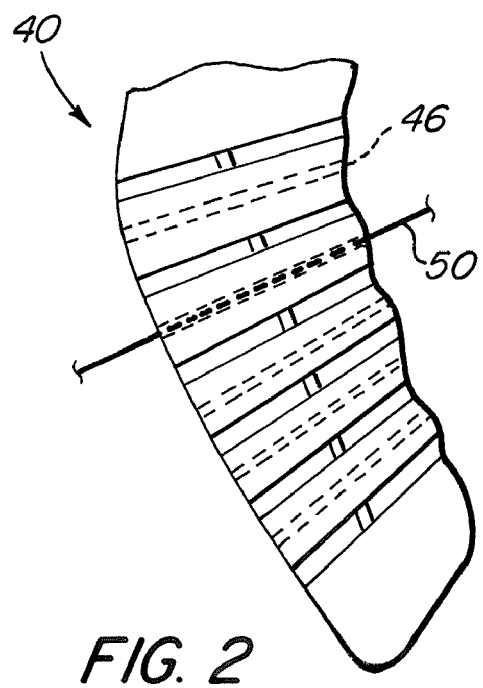
FIG. 2 is an exposed elevational view of a portion of the handle of the drill guide of FIG. 1.

As shown more clearly in FIG. 2, the sleeve 44 has an inner diameter defining a hollow space 46 therein. Accordingly, a drilling member 50, such as, for example, a K-wire, can be inserted into the sleeve 44.

Figure 3A:
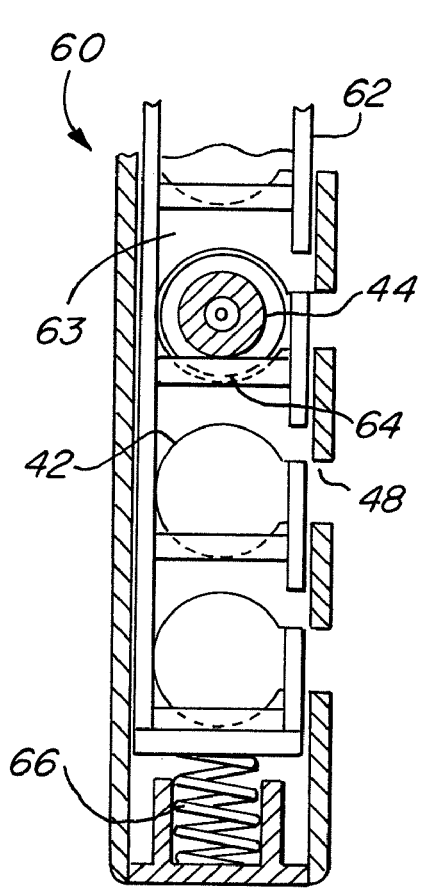
FIG. 3A is a partially cross-sectional side view of the locking mechanism of the drill guide of FIG. 1.
Figure 3B:
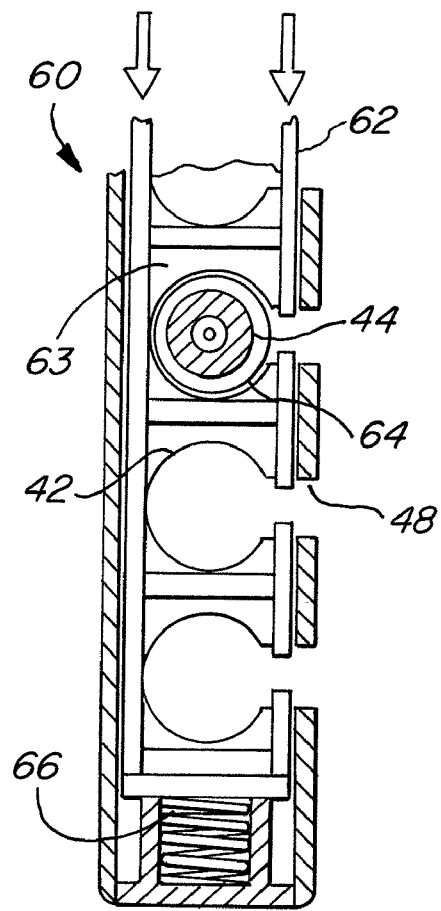
FIG. 3B is a partially cross-sectional side view of the locking mechanism of FIG. 3A in a different position.

In certain advantageous embodiments, a locking mechanism 60 is disposed in the handle in order to secure the sleeve 44 in the channel 42. As illustrated more clearly in FIGS. 3a-3b, in certain advantageous embodiments, the locking mechanism 60 includes a wall member 62 having a plurality of apertures 63 that correspond to the plurality of channels 42. The sleeve 42 has a plurality of ridges 64 such that, when the wall member 62 is in a first position (FIG. 3a), the wall member 62 is disposed between at least two of the ridges 64, thereby preventing the sleeve 44 from moving longitudinally along the channel 42, and thus, the sleeve 44 is locked in place. When the wall member 62 is moved to a second position (FIG. 3b), the wall member 62 moves out from between the ridges 64 and away from the sleeve 44, such that the wall member 62 no longer obstructs the channel 42 and the sleeve 44 is thus free to move longitudinally therein. In certain advantageous embodiments, a biasing force maintains the wall member 62 in one of these positions and, in order for the wall member 62 to move into the other position, a force must be exerted to move the wall member 62 against the bias. In some embodiments, this bias is achieved via a resilient element 66, such as, for example, a spring.

In some advantageous embodiments, the ridges 64 are adapted to inhibit longitudinal movement of the sleeve 44 within the channel 42 in one direction only. In these embodiments, the sleeve 44 may be inserted into the channel 42 and advanced therein even when the wall member 62 is in the first position. In this way, the wall member 62 and the ridges 64 create a ratcheting mechanism by which the sleeve 44 can be advanced through the channel 42.

Figure 4:
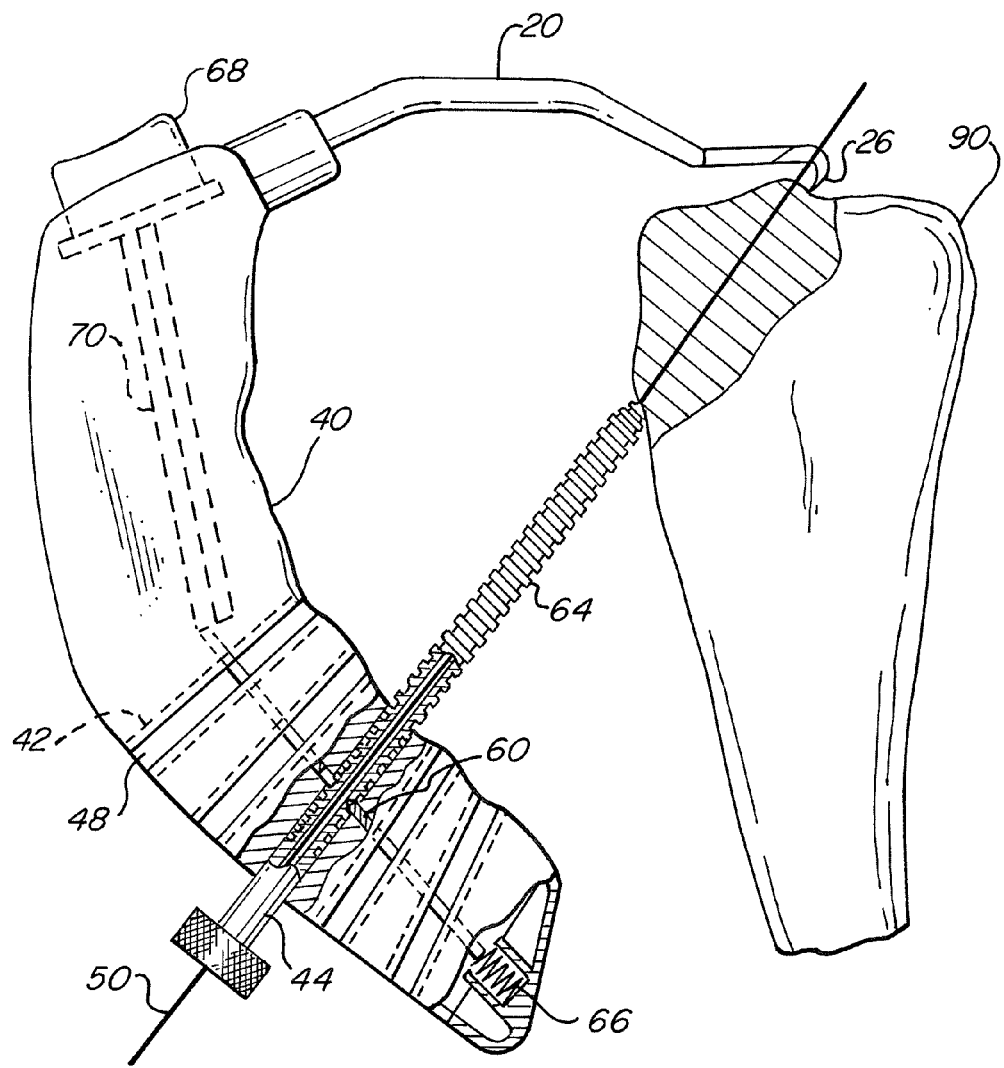
FIG. 4 is an exposed elevational view partially in cross-section of the drill guide of FIG. 1 during the insertion of a K-wire.
Figure 5:
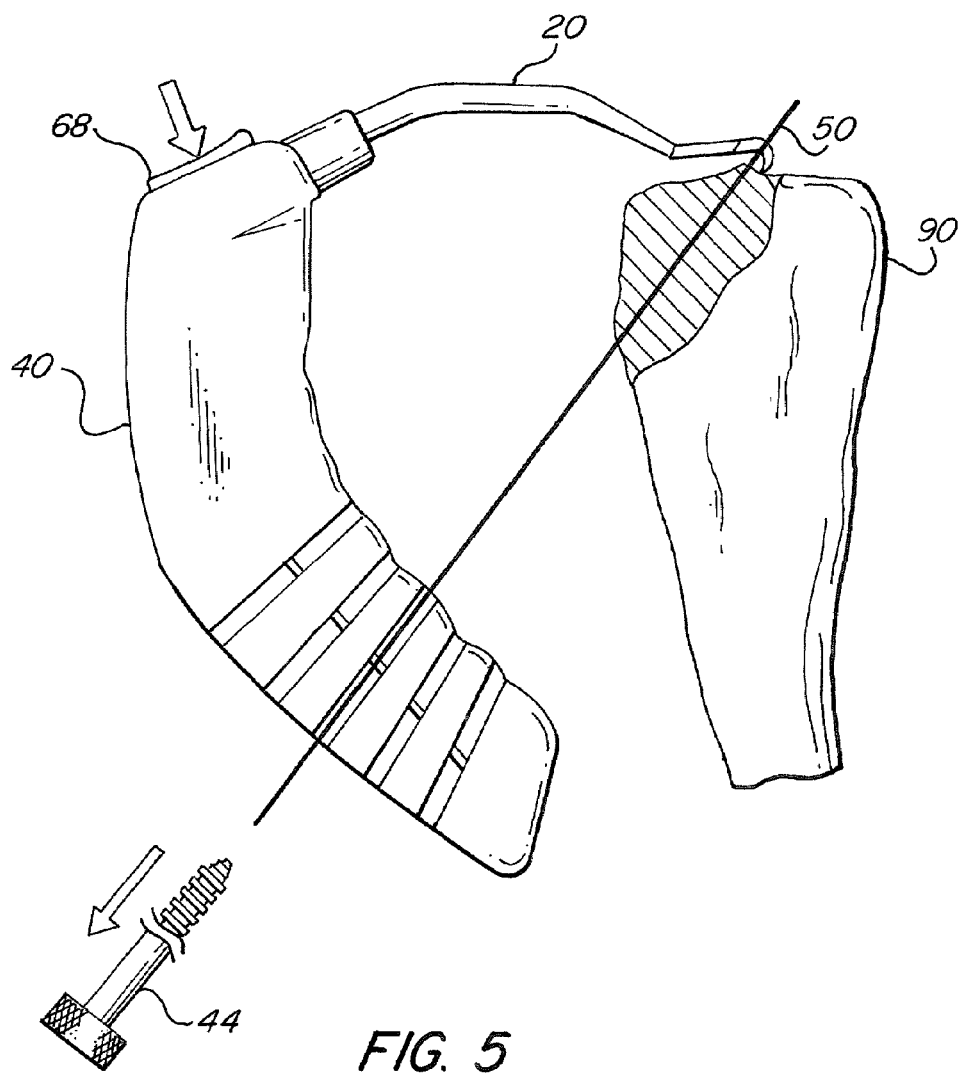
FIG. 5 is an elevational view of the drill guide of FIG. 1 during the withdrawal of a drill sleeve.

Operation of the above described drill guide 10 is illustrated stepwise in FIGS. 4-5. Beginning in FIG. 4, the surgeon begins by inserting the arm 20 into the knee until the hook 26 is disposed against a bone 90. Next, the surgeon moves the wall member 62 into the second position. In certain embodiments, this is accomplished with an actuator 68, such as, for example, a push button. When the push button 68 is depressed, and a push bar 70 is advanced through the handle 40. The push bar 70 exerts a force on the wall member 62, thereby moving the wall member 62 against the bias created by the spring 66. When this occurs, the apertures 63 are aligned with the plurality of channels 42, and thus, the channels 42 are not obstructed. The surgeon then selects the angle at which he or she desires to insert a K-wire 50 into the bone 90 and inserts the sleeve 44 into the appropriately angled channel 42.

Once the sleeve 44 is advanced through the channel 42 to the point at which it is positioned against the anterior of the bone 90, the surgeon then moves the wall member 62 back into the first position. In the embodiment discussed above, this is accomplished by releasing the push button 68. Without the push bar 70 exerting a force upon the wall member 62, the spring 66 biases the wall member 62 into the first position. When this occurs, the wall member 62 engages the ridges 64, locking the sleeve 44 in the channel 42. After the sleeve 44 is locked in the channel 42, the K-wire 50 is inserted into the sleeve 44. The K-wire 50 is then advanced into the bone 90 via drilling or tapping.

Referring to FIG. 5, once the K-wire 50 is disposed in the bone 90, the push button 68 is again depressed, thereby unlocking the sleeve 44, as described above, and the sleeve 44 is withdrawn from the channel 42. The arm 20 is then removed from the knee, and the drill guide is moved away from the patient' body. Subsequently, a cannulated drill bit (not shown) is placed over the K-wire 50, which guides the drill bit through the bone 90 to create the bone tunnel.

If, during the surgical procedure, the surgeon changes his or her mind with respect to the angle at which to insert the K-wire 50, the surgeon can quickly and easily change the angle by unlocking the sleeve 44, withdrawing the sleeve 44 from the channel 42, inserting the sleeve 44 into a different channel 42, and relocking the sleeve 44 into the new channel 42 as described above.

Referring again to FIG. 1, in certain advantageous embodiments, the handle 40 has a plurality of slots 48 that are in communication with the exterior of the handle 40, each of which is sufficiently wide to allow the K-wire 50 to pass through it. Each of the channels 42 is in communication with at least one slot 48. Accordingly, once the K-wire 50 has been inserted into the bone 90, and the sleeve 44 has been withdrawn from the handle 40, the drill guide 10 can simply be rotated away from the K-wire 50 that is still projecting out from the bone 90. As the drill guide 10 is rotated away from the K-wire 50, the K-wire 50 simply passes through the slot 48. Subsequently, the probe arm 20 can be removed from the knee and the drill guide 10 can be back away from the patient's body without fear of bumping the K-wire 50 while doing so and thereby damaging the K-wire 50 or the bone 90 in which the K-wire 50 is disposed.

Figure 6:
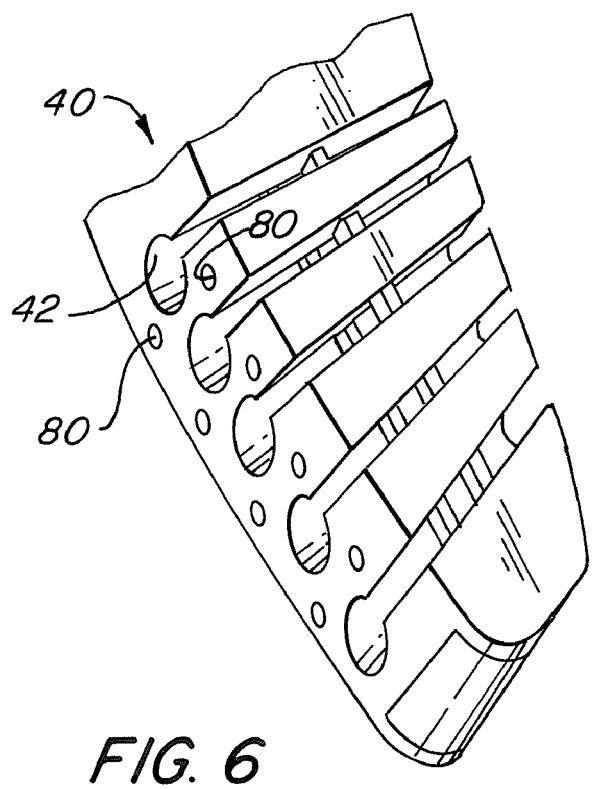
FIG. 6 is a perspective view of a portion of the handle of one embodiment of the drill guide of FIG. 1.

As illustrated in FIG. 6, in some embodiments, the handle 40 may further include ancillary channels 80. The channels 80, located proximate to the channels 42, can be dimensioned to receive a K-wire without the use of the sleeve 44. Accordingly, if, once the surgeon has inserted a K-wire 50 into the bone 90 via the sleeve 44, the surgeon realizes that a K-wire slightly offset from the existing one is desired, the surgeon can accomplish this by simply inserting a K-wire into the ancillary channel 80.

In certain embodiments, similar ancillary channels may be supplied in the handle to permit separate drilling pins (not shown) to be inserted into the bone in order to secure the handle to the bone independently of the K-wire 50 disposed in the sleeve 44. In this manner, these additional channels allow the surgeon to further stabilize the drill guide.

Though a surgeon may have only a single sleeve 44 that he or she uses to insert into the different channels 42, or a plurality of sleeves 44 all having the same inner diameter, in some embodiments, a plurality of sleeves having different inner diameters may be used. In these embodiments, while one sleeve would have an inner diameter such that the sleeve is able to receive K-wires of a certain threshold thickness, a different sleeve would have a different inner diameter. Accordingly, though the surgeon could use any individual sleeve with any K-wire having an outer diameter corresponding to that particular sleeve's threshold diameter or smaller, the surgeon could reduce toggling of the K-wire within the sleeve by selecting a sleeve having an inner diameter that corresponds to the outer diameter of the desired K-wire. Accordingly, the ability to easily insert and remove sleeves as described above also facilitates the selection of sleeves during a procedure that further reduces toggling of the K-wires.

In other embodiments, instead of using a single sleeve 44 that is interchangeably disposable into the different channels 42, a plurality of sleeves 44 may be simultaneously disposed in the plurality of channels 42, as shown in FIG. 7. In these embodiments, even though a surgeon may select the appropriate angle for the bone tunnel after the surgical procedure has begun, the surgeon need not bother with inserting and locking the sleeve 44 during the procedure, but rather, need only insert the K-wire 50 into the appropriate sleeve 44. Moreover, such arrangements may be particularly useful during procedures in which the surgeon changes his or her mind with respect to the desired angle in the middle of the procedure. Because each channel 42 already has a sleeve 44 disposed therein, the surgeon need not withdraw and reinsert, and unlock and relock, the sleeve 44 during the procedure, which could cause undesired movement of the drill guide 10. Accordingly, the drill guide 10, the arm 20 of which is already stabilized against the bone 90, and which may have even already been used to guide another K-wire 50 into the bone 90, will not experience undesired movement, which could jostle the arm hook 26 or the previously inserted K-wire 50.

In some of these embodiments that employ a plurality of sleeves 44 simultaneously disposed in the plurality of channels 42, the sleeves 44 are connected to each other such that they form a single unit 47. With this arrangement, an entire set of sleeves 44 can be removed from, and a different set of sleeves can be inserted into, the plurality of channels 42 quickly and easily. Such arrangements may be particularly useful during procedures in which the surgeon changes his or mind with respect to the desired thickness of the K-wire 50 during the procedure. In such cases, the surgeon can quickly withdraw from the handle 40 a full set of sleeves 44 suited for a particular K-wire thickness and replace it with a full set of sleeves suited for a different K-wire thickness. In this manner, toggling of the K-wire within the sleeve can be reduced while still maintaining both the versatility of the alternate drilling angle arrangement and the convenience and safety of not having to switch a single sleeve from one channel to another.

It should be noted that, while an arrangement employing a sleeve and locking mechanism is generally desired, other arrangements are possible. For example, in certain embodiments, both the channels 42 and the sleeve 44 are threaded. In these embodiments, the sleeve 44 is simply screwed into the desired channel 42. In certain other embodiments, the drilling member 50 itself can be disposed into the channels 42.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A surgical drill guide that forms a tunnel in a bone that passes from a first outer surface of the bone to a second outer surface of the bone, comprising:
   a handle having a plurality of sleeve channels, each channel having an axis, the axes of at least two of the channels being non-parallel with respect to each other;
   an arm having a first end connected to said handle and a second end adapted to contact the bone and secure the surgical drill guide to the second outer surface of the bone; and
   at least one sleeve adapted to receive a drilling member, said sleeve being adapted to be inserted into the plurality of sleeve channels in said handle;
   wherein the drilling member forms a tunnel in the bone that passes from the first outer surface of the bone to the second outer surface of the bone;
   wherein the angle of said sleeve with respect to said handle is variable by disposing said sleeve in different ones of the plurality of channels;
   wherein the second end of said arm includes a mark on at least one surface of the second end that aligns said arm with a particular anatomical landmark.

2. A surgical drill guide as claimed in claim 1, wherein the mark comprises an etched line in at least one surface of the second end.

3. A surgical drill guide as claimed in claim 1, wherein the mark comprises a visual indicator on at least one surface of the second end.

4. A surgical drill guide that forms a tunnel in a bone that passes from a first outer surface of the bone to a second outer surface of the bone, comprising:
   a handle having a plurality of sleeve channels, each channel having an axis, the axes of at least two of the channels being non-parallel with respect to each other;
   an arm having a first end connected to said handle and a second end adapted to contact a bone and secure the surgical drill guide to the second outer surface of the bone; and
   at least one sleeve adapted to receive a drilling member, said sleeve being adapted to be inserted into the plurality of sleeve channels in said handle and at least one of the plurality of sleeve channels receives said sleeve;
   wherein the drilling member forms a tunnel in the bone that passes from the first outer surface of the bone to the second outer surface of the bone;
   wherein the angle of said sleeve with respect to said handle is variable by disposing said sleeve in different ones of the plurality of channels;
   wherein at least one sleeve channel of said plurality of the sleeve channels in said handle comprises at least one slot in communication with an exterior of said handle and said channel along the axis of the at least one sleeve channel.

5. A surgical drill guide that forms a tunnel in the bone that passes from a first outer surface of the bone to a second outer surface of the bone, comprising:
   a handle having a plurality of sleeve channels, each channel having an axis, the axes of at least two of the channels being non-parallel with respect to each other;
   an arm having a first end connected to said handle and a second end adapted to contact a bone and secure the surgical drill guide to the second outer surface of the bone; and
   at least one sleeve adapted to receive a drilling member, said sleeve being adapted to be inserted into the plurality of sleeve channels in said handle;
   wherein the drilling member forms a tunnel in the bone that passes from the first outer surface of the bone to the second outer surface of the bone;
   wherein the angle of said sleeve with respect to said handle is variable by disposing said sleeve in different ones of the plurality of channels;
   wherein said at least one sleeve comprises a plurality of sleeves simultaneously disposed in the plurality of channels;
   wherein said plurality of sleeves are connected to each other.

6. A surgical drill guide that forms a tunnel in a bone that passes from a first outer surface of the bone to a second outer surface of the bone, comprising:
   a handle having a plurality of sleeve channels, each channel having an axis, the axes of at least two of the channels being non-parallel with respect to each other;
   an arm having a first end connected to said handle and a second end that includes a hook that contacts and secures the surgical drill guide to the second outer surface of the bone; and
   at least one sleeve adapted to receive a drilling member that is advanced through the bone from the first outer surface to the second outer surface, said sleeve being adapted to be inserted into the plurality of sleeve channels in said handle;
   wherein the drilling member forms a tunnel in the bone that passes from the first outer surface of the bone to the second outer surface of the bone;
   wherein the angle of said sleeve with respect to said handle is variable by disposing said sleeve in different ones of the plurality of channels.

7. A surgical drill guide as claimed in claim 6, wherein the second end of said arm has an aperture therein that receives the drilling member at the second outer surface of the bone.

8. A surgical drill guide as claimed in claim 7, wherein the aperture is an open-ended hole in the second end of the arm.

* * * * *